United States Patent
Ficke et al.

[11] Patent Number: 6,129,771
[45] Date of Patent: Oct. 10, 2000

[54] GEL CANDLE AND METHOD OF MAKING

[75] Inventors: Geoffrey T. Ficke, Cincinnati, Ohio; Vicky B. McWilliams, Marble Falls, Tex.

[73] Assignee: Aunt Bee's, Inc., Marble Falls, Tex.

[21] Appl. No.: 09/281,333

[22] Filed: Mar. 30, 1999

[51] Int. Cl.$^7$ ....................................................... C10L 5/00
[52] U.S. Cl. ........................... 44/275; 431/126; 431/288; 44/265
[58] Field of Search ...................... 44/275, 265; 431/126, 431/288

[56] References Cited

U.S. PATENT DOCUMENTS

| | | |
|---|---|---|
| D. 231,135 | 4/1974 | Marcum . |
| D. 387,446 | 12/1997 | Bell et al. . |
| 3,388,960 | 6/1968 | Cangialosi ............................. 431/126 |
| 3,434,789 | 3/1969 | Haller . |
| 3,790,332 | 2/1974 | Woollard . |
| 4,035,138 | 7/1977 | Walters . |
| 4,110,066 | 8/1978 | Murphy . |
| 4,568,270 | 2/1986 | Marcus et al. ......................... 431/126 |
| 5,578,089 | 11/1996 | Elsamaloty ............................... 44/275 |
| 5,843,194 | 12/1998 | Spaulding ............................... 44/275 |
| 5,879,694 | 3/1999 | Morrison et al. ....................... 424/405 |

FOREIGN PATENT DOCUMENTS

| | | |
|---|---|---|
| 2261135 | 6/1974 | Germany . |
| 2806182 | 8/1978 | Germany . |
| 7305625 | 10/1974 | Netherlands . |

OTHER PUBLICATIONS

Emory Candle Wonderland catalog, Mar. 1, 1968, Item No. 605.
American Candle Co., Inc. catalog, craftsmen in candles, Aug. 1966, Item No WS–299.

*Primary Examiner*—Jacqueline V. Howard
*Attorney, Agent, or Firm*—Akin, Gump, Strauss, Hauer & Feld, LLP

[57] ABSTRACT

A multi-layer gel candle includes a substantially transparent container, such as a glass tumbler, in which multiple layers of mineral oil-based gel are poured in selective layer patterns including multiple layers with parallel interfaces and multiple layers with intersecting interfaces between layers. Each gel layer may be provided with colorant and fragrance compositions mixed thereinto, as well as light reflective or visual effect enhancing particulates. Striking visual effects and fragrance effects are obtained.

29 Claims, 3 Drawing Sheets

GEL CANDLE AND METHOD OF MAKING

FIELD OF THE INVENTION

The present invention pertains to a candle and method of making same characterized by a transparent container in which layers of gel material are disposed in various patterns and include minute gas bubbles and/or decorative particulate matter distributed throughout the gel layers.

BACKGROUND OF THE INVENTION

Candles, produced and used for purposes of giving light, heat, scent or for celebration or votive purposes, are ubiquitous. Candles which are adapted to produce scent and/or are used for decorations for various purposes are particularly popular. The development of gel material from hydrocarbon-based stock suitable for use in candles has enhanced the aesthetic appeal of candles in one respect since the gel hydrocarbon based stock provides the advantage of transparency. Moreover, such gel materials may be adapted to incorporate fragrance compositions, colorants, dispersed decorative particulates and other active and/or inert components. The present invention has been developed with a view to providing a gel candle and a method of making a gel candle which utilizes the advantages of hydrocarbon based gel formulations in ways heretofore unappreciated by the art.

SUMMARY OF THE INVENTION

The present invention provides an improved gel candle and a method of making same.

In accordance with one aspect of the present invention, a gel candle is provided which includes a transparent container, preferably a tempered glass tumbler, for example, in which multiple layers of clear or colored gel material are disposed to provide a candle which is particularly decorative and attractive when lit or otherwise.

In accordance with another aspect of the present invention, a multi-layer gel candle is provided wherein fine gas bubbles, minute or beadlike particles may be dispersed throughout the gel layers. Moreover, additional light reflecting and fluorescent particulates, such as minute metallic particles or flakes or fluorescent pigments may also be distributed in varying densities throughout one or more of the gel layers.

Still further, the present invention provides a single or multi-layer gel candle in which the gel layers have mixed therein colorants or dyes as well as fragrance compositions to further enhance the aesthetic appeal of the candles.

The present invention also provides a method of making a multi-layer gel candle wherein the candle layers may be oriented such as to provide different geometric patterns. Discrete gel layers are preferably formed by pouring successive layers of gel material when flowable, into the candle container, and allowing each of the gel layers to substantially solidify and then pouring additional gel layers into the container to form the finished candle product.

Those skilled in the art will recognize the above-noted advantages and superior features of the present invention together with other important aspects thereof upon reading the detailed description which follows in conjunction the drawing.

DETAILED DESCRIPTION OF PREFERRED EMBODIMENTS

Figure 1:
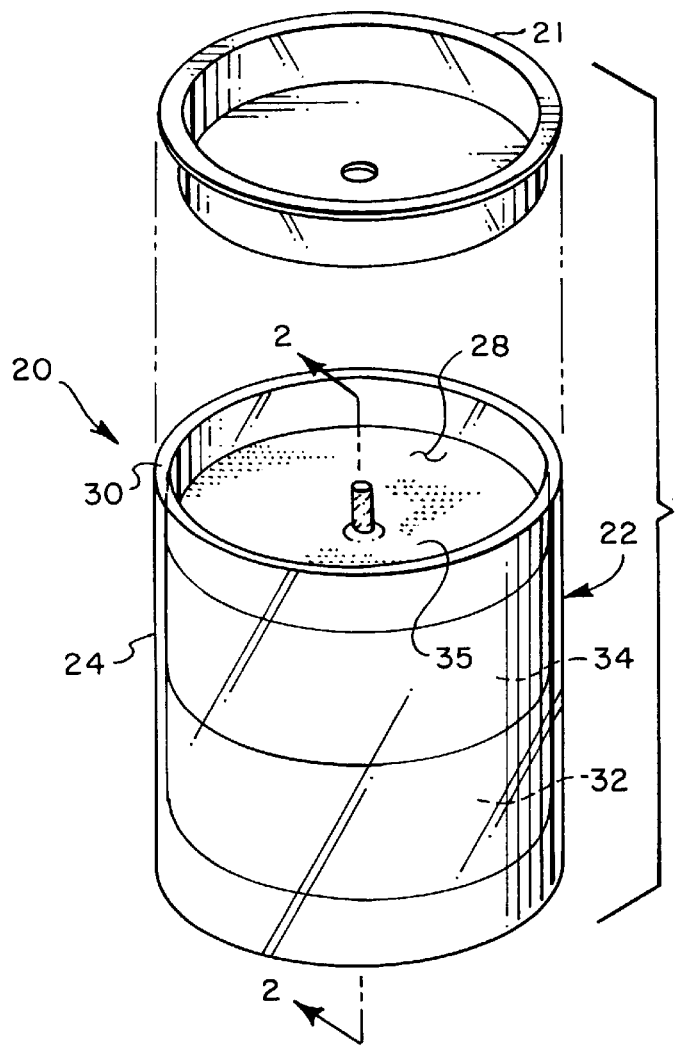
FIG. 1 is a perspective view of a containerized gel candle in accordance with one preferred embodiment of the present invention.

In the description which follows, like elements are marked throughout the specification and drawing with the same reference numerals, respectively. The drawing figures are not necessarily to scale and certain features of the invention may be shown and/or described in somewhat generalized form or terms in the interest of clarity and conciseness.

Referring to FIG. 1, there is illustrated a containerized gel candle in accordance with the present invention and generally designated by the numeral 20. The gel candle 20 is containerized in a transparent container 22, preferably comprising a cylindrical tempered glass tumbler or the like having a cylindrical side wall 24, see FIG. 2, integral with a generally planar cylindrical bottom wall 26 and defining an interior cavity 28 which opens to an upper peripheral rim 30. One preferred size for the container 22 is a glass tumbler having an outside diameter of about 3.15 inches and an overall height of about 3.50 inches. However, containers of other sizes and configurations may be used for the gel candle of the present invention. A removable clear plastic pan shaped protective cover 21 may be used to protect the gel layers until the candle 20 is placed in use.

Figure 2:
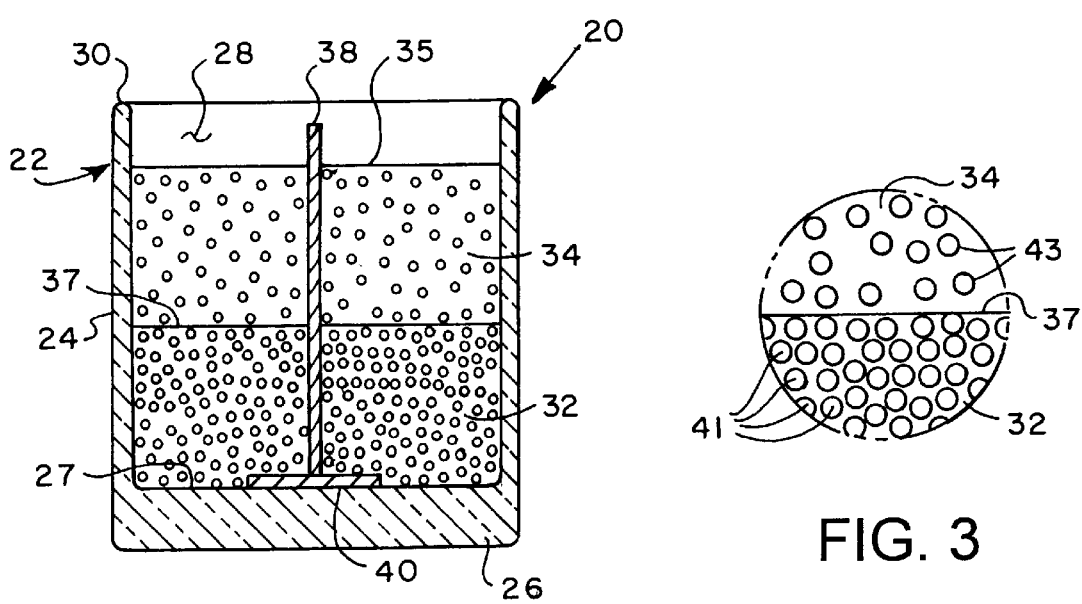
FIG. 2 is a central section view taken generally along the line 2—2 of FIG. 1.

As shown in FIGS. 1 and 2, the candle 20 includes multiple layers of gel material 32 and 34, which may be of equal height or thickness or of selectively varied thicknesses. The gel layer 34 is delimited by a top surface 35 of the candle which is preferably disposed about 0.75 inches from the rim 30. The gel layers 32 and 34 are contiguous at an interface 37, FIGS. 2 and 3. A conventional candle wick 38 is preferably centered in the container 22 and extends from inside surface 27, FIG. 2, of the bottom wall 26 to a point about 0.25 inches above the top surface 35. The wick 38 may be connected to a metal pan or clip 40 which rests on the wall surface 27. A wick size up to about two mm diameter is preferable. The clip or pan 40 may be a circular disk having a diameter of about twenty mm, for example. A zinc-cored wick is preferable for the wick 38 since this type of wick will remain erect when the gel composition forming the layers 32 and 34 is poured into the container 22, using a preferred method of making the candle 20 in accordance with the invention.

The candle layers 32 and 34 are each preferably formed of a gelled hydrocarbon-base, preferably mineral oil. One preferred type of gel composition used for the candle layers 32 and 34, as well as other candle embodiments described hereinbelow, is sold under the trademark VERSAGEL by Penreco Division of the Pennzoil Company, Karns City, Pa. The specific composition may be varied depending on the amount of fragrance composition introduced into the gel layers and in accordance with the concentration of other particulates and/or pigments introduced into the gel. VESAGEL CHP grade gel compositions are preferable for suspension of decorative particulates and pigments within the gel layers.

Preferred mineral oil-based gel compositions for use with the candles of the present invention typically include a predetermined density of gas bubbles entrapped in the gel material, as produced. This bubble concentration or density may be increased or decreased by heating the gel material to liquefaction and stirring the material. Without injection of a bubble forming gas into the gel material, heating and stirring the gel material tends to reduce the gas bubble density. Reduced gas bubble density may be offset by introducing certain particulates, for decorative purposes into the gel material. Various fragrance compositions may be introduced into and stirred throughout the gel material. Various colorants or dyes may also be introduced into and stirred or mixed with the gel material for aesthetic purposes.

Figure 3:
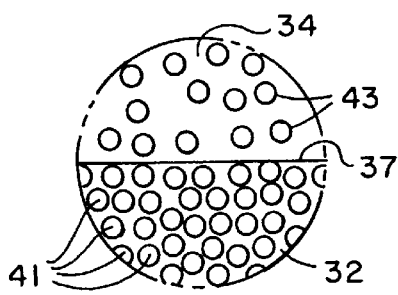
FIG. 3 is a detail view on a larger scale showing the distribution of bubbles and bubble densities in the multiple gel layers of the candle shown in FIGS. 1 and 2.

Referring to FIG. 3, the candle layer 32, formed of the above-mentioned gel material, includes plural gas bubbles 41 dispersed throughout and of a predetermined distribution or density produced by one or more of the techniques mentioned above. The candle layer 34 includes a distribution of gas bubbles 43 which is less dense than the candle layer 32 to provide a pleasing visual effect. The candle layers 32 and 34 may be colored to suit one's aesthetic tastes by introducing a suitable dye or pigment of desired color into a quantity of the gel material forming each of the layers 32 and 34, prior to introducing such gel material into the container 22. Suitable dye or pigment materials which may be used with the gel material mentioned above are available from Pylam Products Company, Incorporated, Tempe, Ariz. under the tradename PYLOWAX. Accordingly, the candle 20 may be provided in one or more layers of at least translucent gel material, depending on the bubble density of the bubbles 41 or 43 and wherein the layers are colored to suit one's tastes. A preferred method of making the candle 20 will be described in further detail hereinbelow.

Figure 4:
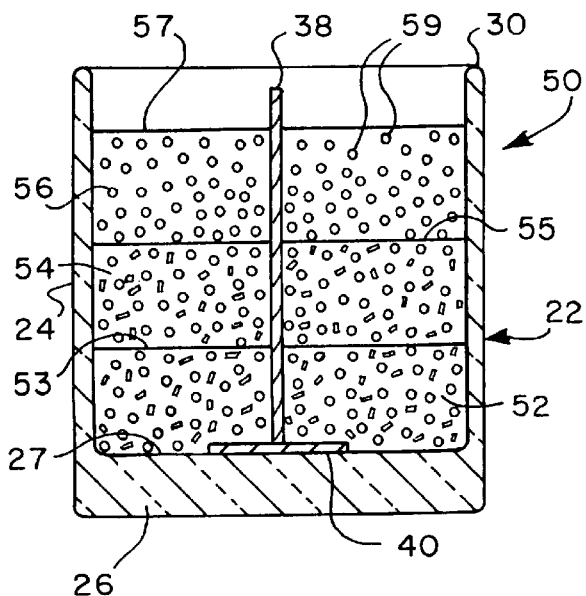
FIG. 4 is a central longitudinal section view of a first alternate embodiment of a candle in accordance with the invention.
Figure 5:
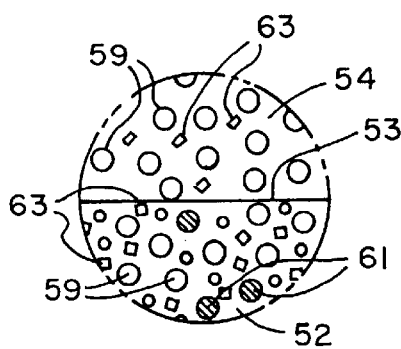
FIG. 5 is a detail view on a larger scale showing the distribution and density of certain particulates mixed in the gel layers of the candle of FIG. 4.

Referring now to FIGS. 4 and 5, an alternate embodiment of a candle in accordance with the present invention is illustrated and generally designated by the numeral 50. The candle 50 is substantially like the candle 20 and utilizes a container 22 and a wick 38. However, the candle 50, as illustrated, is provided with three layers, 52, 54 and 56 of gel material of the type described above. The layers 52, 54 and 56 are separated, respectively, by generally parallel interfaces 53 and 55, as indicated in FIG. 4. An upper, generally planar surface 57 delimits the gel layer 56, as indicated.

In order to further enhance the aesthetic appeal of a gel candle in accordance with the invention, the gel materials making up the layers 52, 54 and 56 may be provided of different colors, using a colorant or dye such as of the type mentioned hereinabove in selected colors and at least one of the layers may be provided with a fragrance composition mixed into the gel material before introducing the gel material into the container 22. Suitable fragrance compositions which may be used with the gel candles of the present invention are available from AFF International, Marietta, Ga., for example. A typical fragrance material which may be used with the candles 20 or 50 is Lavender Fragrance No. 92350, for example, which material is a colorless liquid having a specific gravity of about 0.866 and insoluble in water. Fragrance densities of from 0%–6% may be used with the VERSAGEL gel compositions. A fragrance with a non-polar or hydrocarbon compatible characteristic is preferred since it does not deteriorate the gel strength and has excellent solubility in the above-referenced gel material. Fragrance materials having flash points of 170° F. or higher are preferred with the use of the above-mentioned gel compositions. Blendability may be tested by mixing percentages by weight of 25% fragrance composition and 75% mineral oil or 75% fragrance composition and 25% mineral oil. If blending is substantial at either percentage of fragrance and mineral oil, the nonpolar character of the fragrance composition is suitable for use with the above-mentioned gel materials.

Another important aspect of a gel candle in accordance with the invention is the provision of light reflecting or reradiating particulates dispersed throughout one or more of the gel layers, such as the layers 52 and 54 by way of example. As shown in FIG. 5, gel layer 52, has distributed throughout gas bubbles 59. However, in order to modify the appearance of the bubble density or translucency of the gel layer 52, other materials may be introduced into and distributed throughout the gel layer including clear, translucent or opaque and colored or non-colored glass spheres 61, for example. The glass spheres 61 are preferably of about 0.015" to 0.125" diameter and may be solid or hollow. Other transparent, translucent or opaque materials, such as sea shells or marbles may be used in place of the spheres 61.

Still further, the candle layer 52, as well as the layer 54, may have dispersed throughout light reflecting or fluorescent pigments or so called "glitter" particles 63. Suitable materials for use as the particulates 63 include those available from John Mazzacca Co. of Wayne, N.J. In addition to the reflective particulates 63 distributed throughout the gel or candle layer 54, this layer is also provided with gas bubbles 59 of suitable density controlled in accordance with a method of making the candle 50 to be described further herein.

Figure 6:
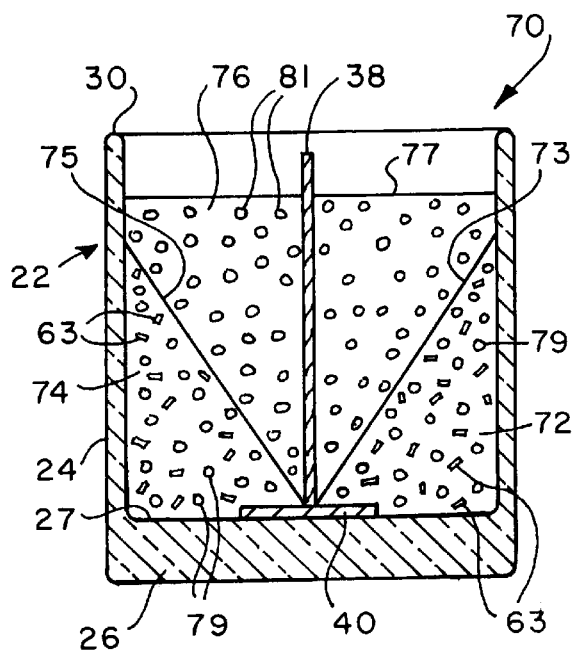
FIG. 6 is a central longitudinal section view of a second alternate embodiment of a gel candle in accordance with the present invention.

Referring now to FIG. 6, another embodiment of a gel candle in accordance with the invention is illustrated and generally designated by the numeral 70. The candle 70 is also provided with multiple layers of gel material disposed in a container 22. However, the candle layers for the candle 70 are arranged substantially different from the layers of gel material used in the candles 20 or 50. As shown in FIG. 6, the candle 70 is provided with first, second and third layers 72, 74 and 76 of gel material. Candle layer 72 is contiguous with candle layer 76 at a planar interface 73 and candle layer 74 is contiguous with candle layer 76 at a planar interface 75. The top surface 77 of layer 76 is generally planar and parallel to bottom wall surface 27. A wick 38 is provided for candle 70 and extends from wick holder or pan 40 substantially through the layer 76. When viewed in the direction indicated in FIG. 6, the layers 72 and 74 form a V-shaped geometric pattern and when viewed in directions normal to the plane of the view of FIG. 6, the periphery of each of interfaces 73 between the layers 72 and 76 and the interface 75 between the layers 74 and 76 take on a partial somewhat elliptical shape.

Impressive visual effects are obtained with the candle 70 by introducing colorants or dyes into the layers 72, 74 and 76 which are compatible with each other but which are of different hues, for example. The densities of gas bubbles 79 in the layers 72 and 74 may be varied from the density or distribution of gas bubbles 81 in the layer 76. Still further, decorative materials, such as the above-mentioned particles 63 may be introduced into and dispersed throughout one or more of the layers 72, 74 and 76.

Figure 7:
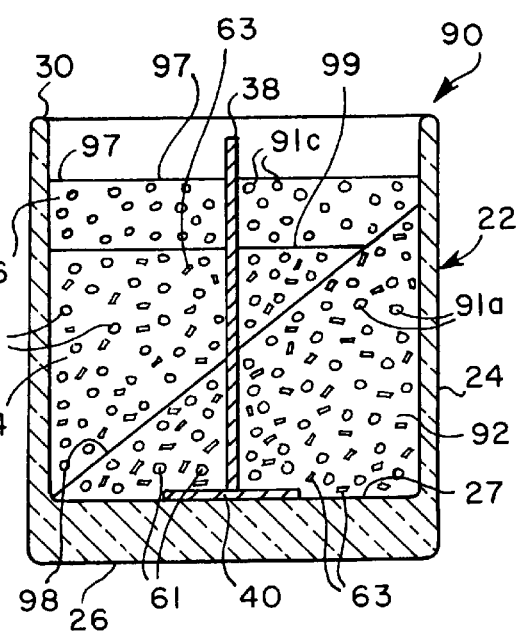
FIG. 7 is a central longitudinal section view of a third alternate embodiment of a gel candle in accordance with the present invention.

Referring now to FIG. 7, yet another embodiment of a candle in accordance with the invention is illustrated and generally designated by the numeral 90. The candle 90 is characterized by a container 22 in which a first gel candle layer 92 is formed and is contiguous with layers 94 and 96 at a generally planar interface 98. Layer 92 extends across the bottom wall surface 27 and is formed such that interface 98 is disposed in a plane intersecting bottom wall surface 27 at about a 45° angle. A top surface 97 of gel layer 96 is generally parallel to the inner wall surface 27 of container bottom wall 26. Gel layers 94 and 96 are contiguous at an interface 99, preferably parallel to surface 97. A wick 38 extends through all of the multiple layers 92, 94 and 96 of candle 90. The visual appeal of the candle 90 may be enhanced by varying the densities of gas bubbles 91a, 91b and 91c distributed throughout the multiple layers 92, 94 and 96. Particulates such as the aforementioned glass beads 61, and/or reflective or light reradiating particulates, such as the particles 63 may be introduced into any one or all of the layers 92, 94 and 96. The colors of the layers 92, 94 and 96 may be selectively varied. Selected fragrance compositions may be mixed into the gel compositions forming the layers 92, 94 and 96 and the fragrances may vary for each layer. In this way, as the candle 90 burns and the layers tend to commingle as the gel composition is consumed down to the respective interfaces 99 and 98, an aroma resulting from emissions from two or more distinct fragrances, which become blended, may be experienced.

Figure 8:
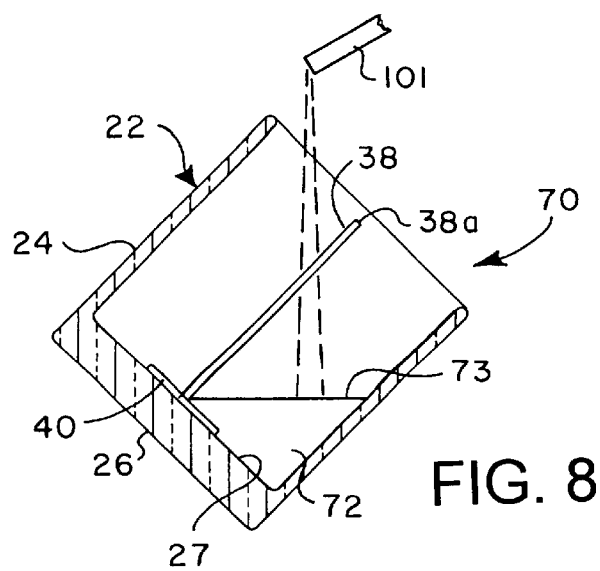
FIGS. 8, 9, and 10 are diagrams illustrating certain steps in a preferred method for making a multi-layered gel candle in accordance with the present invention.
Figure 9:
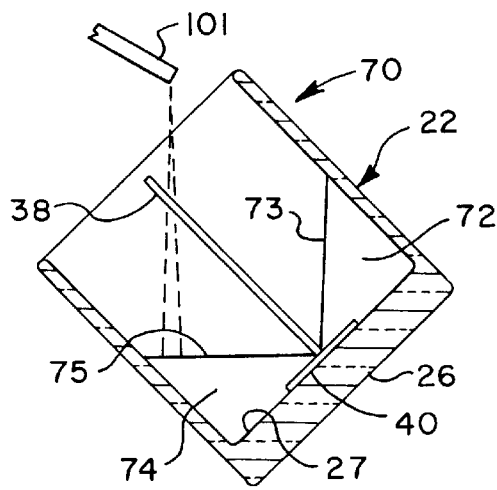
Figure 10:
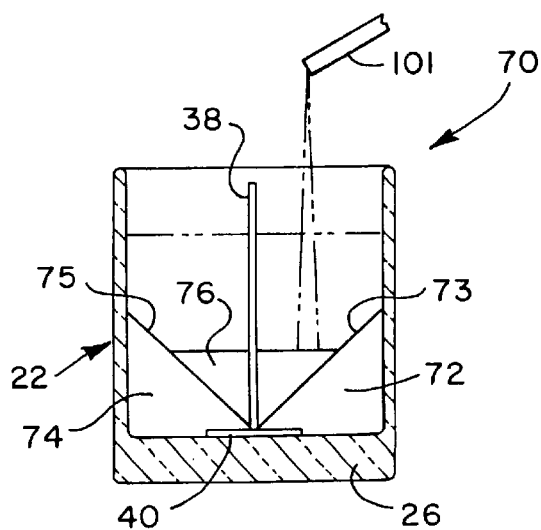

Referring now to FIGS. 8, 9 and 10, a preferred method of making a gel candle in accordance with the invention is illustrated. By way of example, the method will be described in conjunction with making the candle 70. However, those skilled in the art will recognize that the basic steps of the method are carried out for making the candles 20, 50 and 90 also, as well as other candles in accordance with the present invention.

The above-mentioned gel material is preferably ladled out of a storage drum at room temperature into suitable heating, mixing and pouring containers, such as 40–60 quart ceramic or metal pots, not shown, each having a pouring spout 101. Sufficient quantities of gel material are introduced into the mixing and pouring pots of the capacities mentioned above for pouring respective layers of relatively large numbers of candles of container sizes mentioned above. Once the gel material has been deposited into a mixing and pouring pot, the gel material is heated to a temperature in the range of about 200° F. to 210° F., at which temperature materials as described hereinabove may be added. Preferably colorants or powdered dye materials used in providing the colors of the respective candle layers are mixed into the heated gel material initially, followed by the addition of the fragrance compositions and the particulate materials to be added. Pouring of the candle layers may begin while the gel material is held in a temperature range of about 185° F. to 200° F. If gas or air bubble density is to be increased, the temperature of the gel material is lowered to about 170–190° F., whereupon additional bubbles may be generated by injecting gaseous material or by substantial turbulent mixing of the gel material. The temperature of the gel material is then increased or held at about 185° F. for pouring into a container 22.

As shown in FIG. 8, the gel layer 72 is formed by orienting the container 22 at an angle, preferably about 45° to the horizon, then pouring the layer 72. The wick 38 is first placed in the container 22 with its pan or holder 40 suitably secured to wall surface 27 by a suitable adhesive, for example. Still further, the wick 38 may be maintained in its desired position by a suitable fixture, not shown, mounted on the container 22 and engageable with the distal end 38a of the wick. Once the layer 72 has been poured, the container 22 is maintained in the position shown in FIG. 8 to allow gel layer 72, including the surface which will form the interface 73, to solidify. Typically, the temperature of the gel for each candle layer is allowed to reduce to about 140° F. before pouring the next candle layer. Moreover, in order to prevent the second layer of gel from invading the first layer, the pouring temperature of the gel forming the second layer is preferably lowered approximately 10° F. to 20° F. from that at which the first or previous layer was poured.

Referring to FIG. 9, it is indicated how the second layer 74 for candle 70 is being poured by introducing a suitable gel composition in a pourable state into the container 22. The container 22 is held at an angle approximately 90° from the angle at which the container was initially set also 45° to the horizon and with rim 30 facing upward in the pouring step of FIG. 8 to allow formation of the layer 74 and a surface which will form the interface 75 between layer 74 and layer 76.

Lastly, referring to FIG. 10, the candle layer 76 is added to the container 22 after allowing the layer 74 to cool to at least about 140° F. The pouring temperature of the gel material forming the layer 76 is also allowed to drop approximately 10° F. to 20° F. from the pouring temperature of gel layer 74 to prevent substantial invasion of the layer 74 by the material which is being poured to form the layer 76. Cooling time for the gel layers at an ambient temperature of about 70° F.–80° F., for quantities of gel material filling a container of the size and type mentioned herein, is preferably set at about one hour per layer to allow sufficient cooling and gellation or solidification of the gel material without risking commingling or invasion by the pourable gel layer which is being added over an already poured gel layer.

Those skilled in the art will appreciate from the foregoing description that a unique gel candle and method of making are provided by the present invention. The size and configuration of the candle container may be varied for aesthetic purposes and the container 22, although a preferred size and shape of container, is exemplary. Striking visual effects produced by the candles 20, 50, 70 and 90 are provided by the multiple gel layers and geometric patterns provided, as well as the colorants or dyes used, the density of air bubbles and the particulates introduced into the respective layers. Still further, the multiple and mixed aromas produced are particularly unique as the respective layers of the candle are consumed in use.

Although preferred embodiments of the invention have been described in detail herein, those skilled in the art will recognize that various substitutions and modifications may be made without departing from the scope and spirit of the appended claims.

What is claimed is:

1. A gel candle comprising:
   a substantially transparent container having a bottom and a side wall defining a cavity and a top rim delimited by said side wall;
   a wick disposed in said container; and
   multiple layers of gel material disposed in said container, said multiple layers are formed one on top of the other and adjacent layers being contiguous at an interface between said adjacent layers, respectively, at least one of said layers encompassing said wick and said multiple layers having distributed throughout gas bubbles of different densities of distribution in respective ones of said multiple layers and producing a visual effect in said multiple layers, respectively.

2. The candle set forth in claim 1 wherein:

at least one of said layers includes a colorant distributed throughout to provide color contrast between said layers.

3. The candle set forth in claim 1 wherein:

at least one of said layers includes light reflecting or reradiating particulates dispersed therein to reflect ambient light and light generated by burning said candle.

4. The candle set forth in claim 1 wherein:

said multiple layers have a different geometric configuration, respectively, and at least two layers of said multiple layers are contiguous with each other at an interface.

5. The candle set forth in claim 4 wherein:

said candle is formed of two layers which are opposed to each other in said container and said candle includes a third layer interposed said two layers and contiguous with said two layers at opposed interfaces.

6. The candle set forth in claim 4 wherein:

one of said layers extends across a major portion of said bottom of said container and forms a generally planar interface with a second layer of gel material disposed in said container and having a top surface generally parallel to said bottom of said container.

7. The candle set forth in claim 1 further including particulates comprising substantially transparent beads.

8. The candle set forth in claim 1 further including particulates comprising light reflecting material.

9. The candle set forth in claim 1 further including particulates comprising fluorescent pigments.

10. The candle set forth in claim 1 wherein:

at least one of said layers includes a fragrance composition mixed therein.

11. The candle set forth in claim 10 wherein:

plural ones of said layers include respective fragrance compositions mixed therein, respectively, of different fragrances.

12. The candle set forth in claim 1 wherein:

a first layer of said candle is formed by heating gel material to a pourable state and pouring said gel material into said container followed by allowing said first layer to solidify, then pouring a second layer of gel material into said container.

13. The candle set forth in claim 12 wherein:

said candle is formed by pouring a third layer of gel material into said container after allowing said second layer to substantially solidify.

14. The candle set forth in claim 13 wherein:

said wick is disposed in said container prior to pouring said first layer.

15. The candle set forth in claim 12 wherein:

the density of gas bubble distribution in said multiple layers, respectively, is reduced by heating said gel composition for each layer.

16. The candle set forth in claim 12 wherein:

the density of gas bubbles in said multiple layers, respectively, is increased by reducing the temperature of said gel material and injecting a gaseous composition into said gel material while mixing said gel material for each layer.

17. A method of making a gel candle wherein said gel candle comprises a substantially transparent container having a bottom and a side wall defining a cavity and a top rim delimited by said side wall, a wick disposed in said container and multiple layers of gel material disposed in said container, at least one of said layers encompassing said wick and selected ones of said multiple layers having distributed throughout gas bubbles of different densities of distribution in each of said selected layers producing a visual effect, said method comprising the steps of:

heating separate quantities of said gel material to a pourable state, respectively, and to selected temperatures to vary the density of distribution of said bubbles in said selected layers;

pouring a first layer of gel material into said container disposed in a predetermined position;

allowing said first layer to cool to substantially solidify said first layer; and pouring at least a second layer of gel material into said container to form said multiple layers, at least one of said first and second layers having bubbles distributed therein of a predetermined density of distribution.

18. The method set forth in claim 17 including the step of:

mixing light reflecting and/or reradiating material into one of said quantities of gel material prior to pouring a layer of said candle from said one quantity.

19. The method set forth in claim 17 including the step of:

mixing a fragrance composition into respective ones of said quantities of gel material prior to pouring said layers.

20. The method set forth in claim 19 wherein:

the fragrance compositions mixed into said quantities of gel material are different from each other.

21. The method set forth in claim 17 including the step of:

mixing colorant materials into at least one of said quantities of gel material prior to pouring said one quantity of gel material into said container to form one of said layers.

22. The method set forth in claim 17 including the step of:

orienting said container in one direction prior to pouring a first layer of gel material and orienting said container in a second direction prior to pouring another layer of said gel material into said container.

23. The method set forth in claim 22 including the step of:

orienting said container in a third direction prior to pouring a further layer of gel material into said container.

24. The method set forth in claim 17 including the step of:

allowing a quantity of gel material to be poured into said container to cool to a temperature range of about 10° F. to 20° F. cooler than the temperature of the previously poured layer of gel material prior to pouring said quantity of gel material.

25. A method of making a gel candle wherein said gel candle comprises a substantially transparent container having a bottom and a side wall defining a cavity and a top rim delimited by said side wall, a wick disposed in said container and multiple layers of gel material disposed in said container, at least one of said layers encompassing said wick and at least one of said layers having distributed throughout at least one of plural and distributed gas bubbles and particulates producing a visual effect, said method comprising the steps of:

heating separate quantities of said gel material to a pourable state, respectively;

orienting said container in one direction prior to pouring a first layer of gel material;

pouring a first layer of gel material into said container while said container is disposed in said one direction;

allowing said first layer to cool to substantially solidify said first layer;

orienting said container in a second direction prior to pouring a second layer of gel material into said container; and pouring a second layer of gel material into said container to form said plural layers.

26. A gel candle comprising:

a substantially transparent container having a bottom and a sidewall defining a cavity and a top rim delimited by said sidewall;

a wick disposed in said container; and multiple layers of gel material disposed in said container comprising first and second layers opposed to each other in said container and a third layer interposed said first and second layers and contiguous with said first and second layers at opposed inclined interfaces, at least a portion of said third layer encompassing said wick.

27. The gel candle set forth in claim 26 wherein:

at least one of said layers having distributed throughout at least one of plural and distributed gas bubbles and particulates producing a visual effect in said at least one layer.

28. A gel candle comprising:

a substantially transparent container having a bottom and a sidewall defining a cavity and a top rim delimited by said sidewall;

a wick disposed in said container; and multiple layers of gel material disposed in said container, at least one of said layers encompassing at least part of said wick, a first layer extending across a major portion of said bottom of said container and forming a generally planar inclined interface with at least a second layer, said second layer having a top surface generally parallel to said bottom of said container.

29. The gel candle set forth in claim 28 wherein:

at least one of said layers having distributed throughout at least one of plural and distributed gas bubbles and particulates producing a visual effect in said at least one layer.

* * * * *